US009486182B2

(12) United States Patent
Katsuyama

(10) Patent No.: US 9,486,182 B2
(45) Date of Patent: Nov. 8, 2016

(54) ULTRASOUND IMAGE GENERATING DEVICE, ULTRASOUND IMAGE GENERATING METHOD, AND PROGRAM

(71) Applicant: FUJIFILM Corporation, Tokyo (JP)

(72) Inventor: Kimito Katsuyama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 473 days.

(21) Appl. No.: 13/826,664

(22) Filed: Mar. 14, 2013

(65) Prior Publication Data
US 2013/0267849 A1 Oct. 10, 2013

Related U.S. Application Data

(63) Continuation of application No. PCT/JP2011/072089, filed on Sep. 27, 2011.

(30) Foreign Application Priority Data

Sep. 27, 2010 (JP) ................................. 2010-215735

(51) Int. Cl.
*A61B 8/00* (2006.01)
*A61B 8/08* (2006.01)

(52) U.S. Cl.
CPC .............. *A61B 8/58* (2013.01); *A61B 8/5207* (2013.01)

(58) Field of Classification Search
USPC ........................................................ 600/443
See application file for complete search history.

(56) References Cited

U.S. PATENT DOCUMENTS

| 6,224,553 B1 * | 5/2001 | Nevo ............................ 600/437 |
| 2003/0092990 A1 * | 5/2003 | Baba ........................ A61B 8/00 600/443 |
| 2005/0148872 A1 * | 7/2005 | Richard .............. G01S 7/52034 600/443 |
| 2008/0242999 A1 * | 10/2008 | Kakee ........................... 600/458 |
| 2010/0076312 A1 | 3/2010 | Katsuyama |

FOREIGN PATENT DOCUMENTS

| JP | 08-317926 | A | 12/1996 |
| JP | 2009-078124 | A | 4/2009 |
| JP | 2009078124 | * | 4/2009 |
| JP | 2010-012157 | A | 1/2010 |
| JP | 2010-099452 | | 5/2010 |

OTHER PUBLICATIONS

Translation of JP2009078124.*
Notification of Reasons for Refusal issued by JPO on Mar. 4, 2014, in connection with corresponding Japanese Patent Application No. 2012-536483.

* cited by examiner

*Primary Examiner* — Serkan Akar
(74) *Attorney, Agent, or Firm* — Jean C. Edwards, Esq.; Edwards Neils LLC

(57) ABSTRACT

This ultrasound image generating device includes an ultrasound probe which transmits ultrasound into a subject, receives reflected sound, and outputs an ultrasound detection signal, the ultrasound image generating device generating a topographical image which represents a shape. The ultrasound image generating device further includes a sound speed value computation unit which computes a sound speed value in a region of interest in the topographical image; and a degree of reliability information generation unit which generates degree of reliability information of the sound speed value on the basis of the sound speed value corresponding to the region of interest.

9 Claims, 11 Drawing Sheets

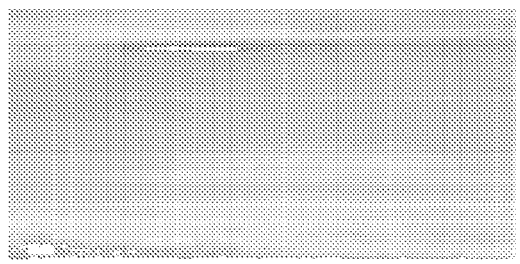
FIG.12
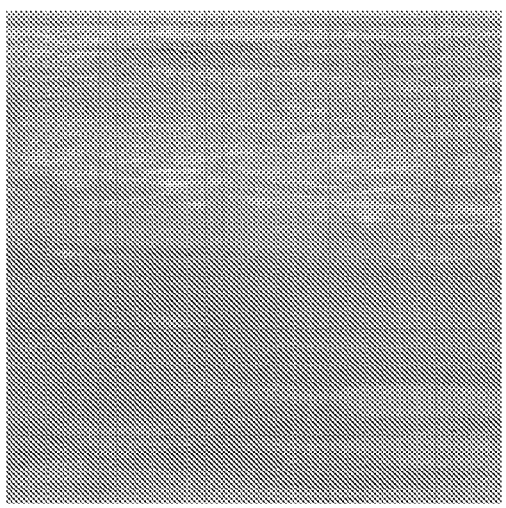
FIG.13
FIG.14

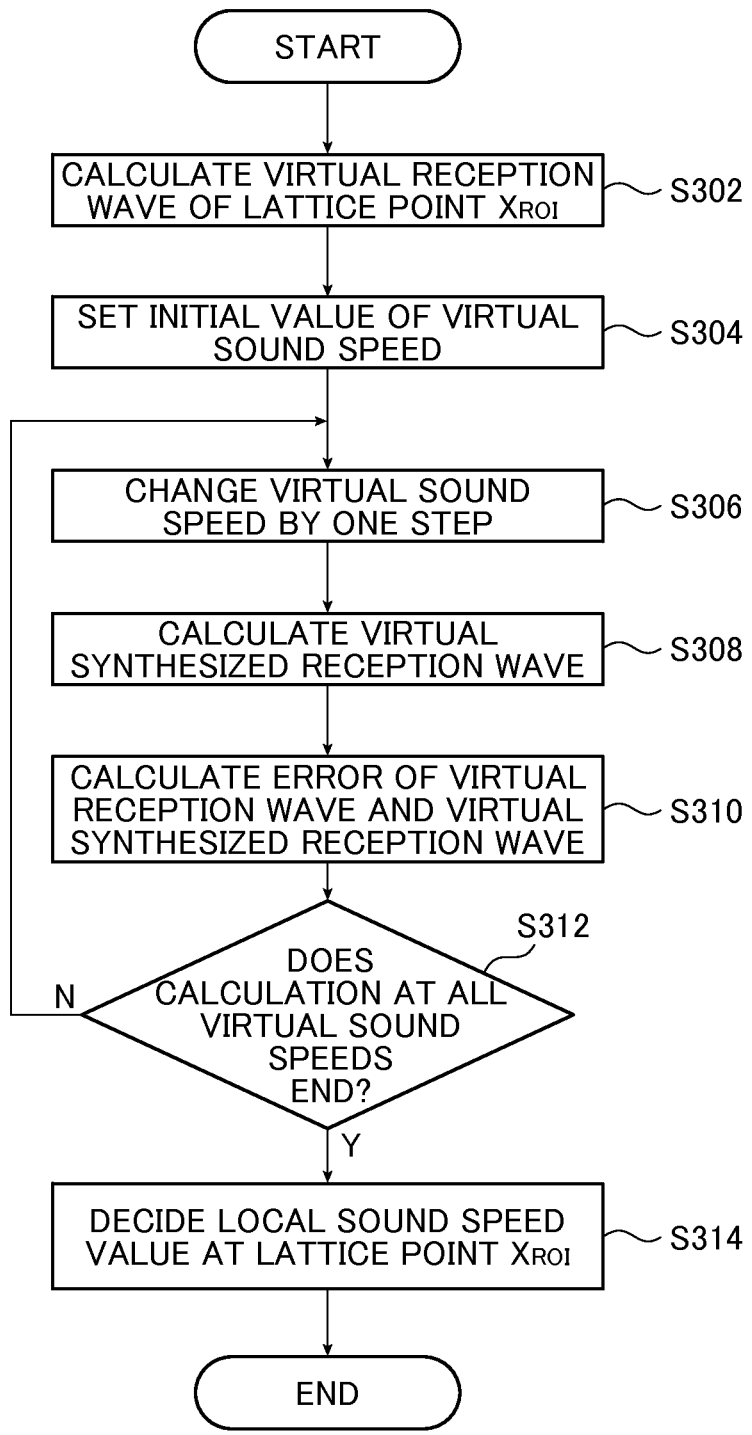

ULTRASOUND IMAGE GENERATING DEVICE, ULTRASOUND IMAGE GENERATING METHOD, AND PROGRAM

CROSS-REFERENCE TO RELATED APPLICATIONS

This application is a continuation application of International Application No. PCT/JP2011/072089, filed Sep. 27, 2011, which was published under PCT Article 21(2) in Japanese, which is based upon and claims the benefit of priority from Japanese Application No. 2010-215735 filed on Sep. 27, 2010, the contents of all of which are incorporated by reference herein in their entirety.

TECHNICAL FIELD

The present invention relates to an ultrasound image generating device, an ultrasound image generating method and a program, which transmit an ultrasonic wave toward a subject, receive a reflected wave and display an image, and in particular, to an ultrasound image generating device, an ultrasound image generating method and a program, which image sound speed of a region of interest and reliability of the sound speed from the received reflected wave.

BACKGROUND ART

Heretofore, as one morphological image of an ultrasound image, a B-mode image (an image in which amplitude of an ultrasonic echo is represented by point luminance) representing a shape is used. In order to achieve high image quality of the B-mode image, a technique is suggested in which a sound speed value is corrected with focus data obtained by setting the sound speed of the subject, thereby improving the focus of the B-mode image. Furthermore, a measurement of a sound speed value in a portion of the subject (hereinafter, referred to as a local sound speed value) is tried.

For example, Patent Literature 1 discloses an ultrasound tomographic device in which focus calculation is performed using an input ultrasonic sound speed value as set sound speed of the whole device, and an ultrasound image is taken using the obtained focus data to correct the set ultrasonic sound speed value (that is, using an ambient sound speed value (hereinafter, sometimes referred to as an optimum sound speed value)), thereby improving the focus.

Patent Literature 2 discloses an ultrasound diagnostic device in which a lattice point set in a region shallower than a region of interest in a subject and an optimum sound speed value in the region of interest are determined using the Huygens principle, a reception wave received from the region of interest when an ultrasonic wave is transmitted toward the region of interest is calculated on the basis of the optimum sound speed value in the region of interest, an assumed sound speed in the region of interest is assumed, a reception wave from each lattice point obtained from the optimum sound speed value at each lattice point on the basis of the assumed sound speed is synthesized to obtain a synthesized reception wave, and a local sound speed value in the region of interest is decided on the basis of the reception wave and the synthesized reception wave.

CITATION LIST

Patent Literature

Patent Literature 1 JP 8-317926 A
Patent Literature 2 JP 2010-99452 A

SUMMARY OF INVENTION

Technical Problems

However, in Patent Literature 1, while the focus of the B-mode image is improved, it is not possible to obtain a sound speed value in an arbitrary region of an image. In Patent Literature 2, while there are disclosures in obtaining the local sound speed value of the region of interest, improving the focus by use of the obtained sound speed value, reconstructing the B-mode image and achieving high image quality, and displaying the B-mode image and the decision result of the local sound speed value in an overlapping manner (for example, changing color or luminance depending on a local sound speed value), there is no disclosure in obtaining reliability of a sound speed value.

An object of the invention is to provide an ultrasound image generating device, an ultrasound image generating method and a program, which obtain not only an ambient sound speed value or a local sound speed value of a region of interest but also reliability thereof, use only the reliable ambient sound speed value or local sound speed value for a focus, or directly display or image and display these values, thereby generating an ultrasound image such that a lesion in a subject is more easily detected.

Solution to the Problems

To achieve the above object, the present invention provides an ultrasound image generating device which has an ultrasound probe which transmits an ultrasonic wave toward a subject, receives a reflected wave and outputs an ultrasonic detection signal, and which generates a morphological image representing a shape, the ultrasound image generating device comprising a sound speed value calculator which calculates a sound speed value in a region of interest of the morphological image; and a reliability information generator which generates reliability information of the sound speed value on the basis of the sound speed value corresponding to the region of interest.

Preferably, further comprising a sound speed image generator which generates a sound speed image on the basis of the sound speed value corresponding to the region of interest, wherein the reliability information generator is adapted to generate the reliability information for each region corresponding to the region of interest of the sound speed image.

Preferably, further comprising a reliability image generator which generates a reliability image on the basis of the reliability information.

Preferably, further comprising an image processor which generates a display image from at least one of the morphological image, the sound speed image and the reliability image; and a display unit which displays the display image.

Preferably, the reliability information is information obtained from each of pixels of the sound speed image and a predetermined range of pixels around each of the pixels.

Preferably, the reliability information is information obtained from each of pixels between a plurality of the sound speed images.

Preferably, the reliability information is measurement error information acquired when a discontinuous point is detected by edge detection processing or gap detection processing on the sound speed image.

Preferably, the sound speed value is an ambient sound speed value, and the sound speed image is an ambient sound speed image.

Preferably, the sound speed value calculator has an ambient sound speed value calculator which calculates an ambient sound speed value, and a local sound speed value calculator which calculates a local sound speed value on the basis of the ambient sound speed value, and the sound speed value is the local sound speed value, and the sound speed image is a local sound speed image.

Preferably, the sound speed value calculator is adapted to obtain a focus index value of each of pixels of the morphological image, or obtain an error of a virtual reception wave and a virtual synthesized reception wave in each of pixels for each of assumed local sound speeds from each of the pixels and a predetermined range of pixels around the each of the pixels for each of set sound speeds, and the reliability information generator is adapted to generate reliability information on the basis of the focus index value for each of the set sound speeds or the error for each of the assumed local sound speeds.

Preferably, further comprising a sound speed image generator, wherein the sound speed value calculator is adapted further to calculate an ambient sound speed value or a local sound speed value in a region of interest of the morphological image on the basis of the focus index value for each of the set sound speeds and the error for each of the assumed local sound speeds, the sound speed image generator is adapted to generate a sound speed image on the basis of the ambient sound speed value or the local sound speed value corresponding to the region of interest, and the reliability information generator is adapted further to generate the reliability information for each region corresponding to the region of interest of the sound speed image.

Preferably, further comprising a reliability image generator which generates a reliability image on the basis of the reliability information.

Preferably, further comprising an image processor which generates a display image from at least one of the morphological image, the sound speed image and the reliability image; and a display unit which displays the display image.

Preferably, the morphological image, and the sound speed image or the reliability image are displayed on the display unit in an overlay manner.

Preferably, display is performed in a state where pixels having the reliability information lower than a predetermined value among the pixels of the reliability image are masked.

Also, to achieve the above object, the present invention provides an ultrasound image generating method which transmits an ultrasonic wave toward a subject, receives a reflected wave, and generates a morphological image representing a shape, the ultrasound image generating method comprising a sound speed value calculating step of calculating a sound speed value in a region of interest of the morphological image; and a reliability information generating step of generating reliability information of the sound speed value on the basis of the sound speed value corresponding to the region of interest.

Preferably, further comprising a sound speed image generating step of generating a sound speed image on the basis of the sound speed value corresponding to the region of interest, wherein the reliability information generating step generates the reliability information for each region corresponding to the region of interest of the sound speed image.

Preferably, the sound speed value calculating step obtains a focus index value of each of pixels of the morphological image for each of set sound speeds, or obtains an error of a virtual reception wave and a virtual synthesized reception wave in each of the pixels for each of assumed local sound speeds from each of the pixels and a predetermined range of pixels around each of the pixels, and the reliability information generating step generates reliability information on the basis of the focus index value for each of the set sound speeds or the error for each of the assumed local sound speeds.

Preferably, further comprising a sound speed image generating step, wherein the sound speed value calculating step calculates an ambient sound speed value or a local sound speed value in a region of interest of the morphological image on the basis of the focus index value for each of the set sound speeds or the error for each of the assumed local sound speeds, the sound speed image generating step generates a sound speed image on the basis of the ambient sound speed value or the local sound speed value corresponding to the region of interest, and the reliability information generating step generates reliability information for each region corresponding to the region of interest of the sound speed image.

Preferably, further comprising a reliability image generating step of generating a reliability image on the basis of the reliability information.

Also, to achieve the above object, the present invention provides a program which causes a computer to execute the steps of the ultrasound image generating method according to any one of the above described method.

Also, to achieve the above object, the present invention provides a computer-readable recording medium having the program described above recorded thereon.

Advantageous Effects of the Invention

According to the invention, it is possible to provide an ambient sound speed image or a local sound speed image and a reliability image such that a lesion in a subject is more easily detected, without using a configuration in which a dedicated ultrasonic wave for measuring an ambient sound speed value or a local sound speed value is transmitted and received.

BRIEF DESCRIPTION OF DRAWINGS

FIG. 12 is an explanatory view illustrating another example of display of a sound speed image.

FIG. 13 is an explanatory view illustrating another example of display of a sound speed image.

FIG. 14 is an explanatory view illustrating another example of display of a sound speed image.

FIG. 18 is a flowchart illustrating an example of processing for calculating a local sound speed value according to the invention.

DESCRIPTION OF EMBODIMENTS

Hereinafter, an ultrasound image generating device according to the invention which executes an ultrasound image generating method according to the invention will be described in detail on the basis of preferred embodiments illustrated in the accompanying drawings. In the following embodiments, a case where a B-mode image is used as a morphological image will be described.

Figure 1:
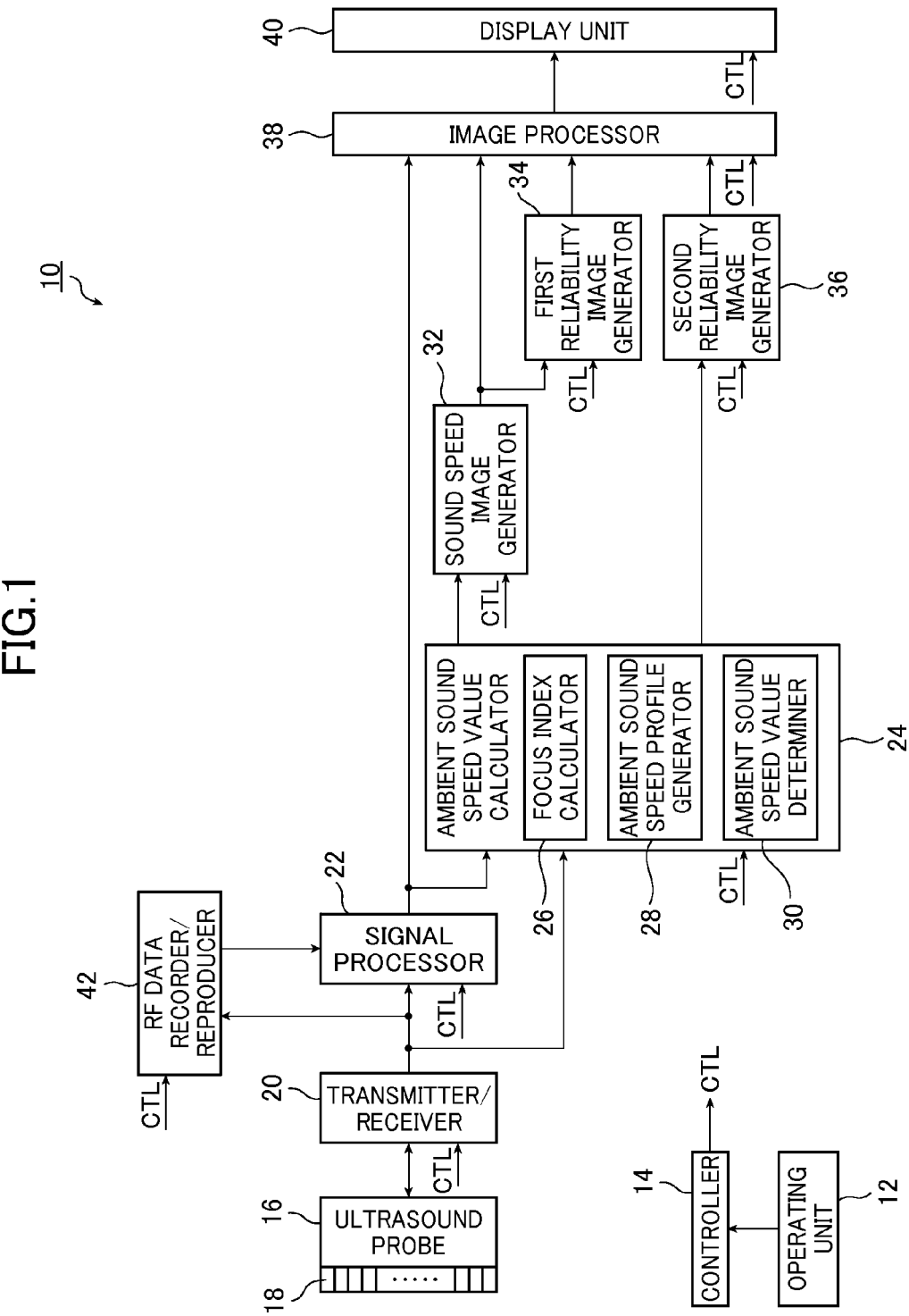
FIG. 1 is a block diagram illustrating an example of the configuration of an ultrasound image generating device according to a first embodiment of the invention which executes an ultrasound image generating method according to the invention.

FIG. 1 is a block diagram illustrating the configuration of a first embodiment of an ultrasound image generating device according to the invention. In the ultrasound image generating device of the first embodiment, a sound speed image and a reliability image are generated using an ambient sound speed value as a sound speed value.

The ultrasound image generating device 10 illustrated in FIG. 1 includes an operating unit 12, a controller 14, an ultrasound probe 16, a transmitter/receiver 20, a signal processor 22, an ambient sound speed value calculator 24, a sound speed image generator 32, a first reliability image generator 34, a second reliability image generator 36, an image processor 38, a display unit 40, and an RF data recorder/reproducer 42. The ambient sound speed value calculator 24 includes a focus index calculator 26, an ambient sound speed profile generator 28, and an ambient sound speed value determiner 30.

The operating unit 12 is used when an operator performs various operations on the ultrasound image generating device 10, and outputs operation information. The configuration of the operating unit 12 is not particularly limited, and various known operating devices, such as a keyboard, a mouse and a touch panel, may be used.

The controller 14 controls the operation of each unit of the ultrasound image generating device 10. Furthermore, the controller 14 outputs a control signal (CTL) to each unit such that various kinds of processing are performed in accordance with the operation information, and also sets a set sound speed or a reception delay pattern for obtaining an ambient sound speed value in the transmitter/receiver 20 described below.

The ultrasound probe 16 is a probe which is used in contact with the subject, and includes a plurality of ultrasound transducers 18 constituting a one-dimensional or two-dimensional transducer array. In each ultrasound transducer 18, an ultrasonic beam is transmitted toward the subject on the basis of an actuation signal which is applied from the transmitter/receiver 20, an ultrasonic echo which is reflected from the subject is received, and a detection signal is output.

Each ultrasound transducer 18 includes a vibrator in which electrodes are formed at both ends of a piezoelectric material (piezoelectric body). As a piezoelectric body which constitutes the vibrator, for example, a piezoelectric ceramic such as PZT (Pb (lead) zirconate titanate), or a polymer piezoelectric element such as PVDF (polyvinylidene difluoride), may be used. If an electric signal is sent to the electrodes of the vibrator to apply a voltage across the electrodes, the piezoelectric body expands and contracts, whereby ultrasonic waves are generated in each vibrator with the expansion and contraction of the piezoelectric body. For example, if a pulsed electric signal is sent to the electrodes of the vibrator, a pulsed ultrasonic wave is generated, and if a continuous-wave electric signal is sent to the electrodes of the vibrator, a continuous-wave ultrasonic wave is generated. The ultrasonic waves generated in the respective vibrators are synthesized to form an ultrasonic beam. If an ultrasonic wave is received by each vibrator, the piezoelectric body of each vibrator expands and contracts to generate an electric signal. The electric signals generated in the respective vibrators are output to the transmitter/receiver 20 as the detection signals of the ultrasonic waves.

As the ultrasound transducer 18, a plurality of kinds of ultrasonic conversion elements which are different from each other in ultrasonic wave conversion method may be used. For example, a vibrator which is constituted by the above-described piezoelectric body may be used as an element which transmits an ultrasonic wave, and an ultrasound transducer of optical detection type may be used as an element which receives an ultrasonic wave. Here, the ultrasound transducer of optical detection type is an ultrasound transducer which converts an ultrasound signal to an optical signal and detects the optical signal, and the example thereof is a Fabry-Perot resonator or a FBG (Fiber Bragg Grating).

The transmitter/receiver 20 includes a transmission circuit, a reception circuit, and an A/D converter.

The transmission circuit generates an actuation signal in accordance with a control signal from the controller 14 and applies the actuation signal to the ultrasound transducer 18. At this time, the transmission circuit delays the actuation signal to be applied to each ultrasound transducer 18, on the basis of a transmission delay pattern selected by the controller 14. That is, the transmission circuit adjusts (delays) the timing of applying the actuation signal to each ultrasound transducer 18 such that ultrasonic waves to be transmitted from the plurality of ultrasound transducers 18 form an ultrasonic beam. Alternatively, the timing of applying the actuation signal may be adjusted such that ultrasonic waves to be transmitted simultaneously from the plurality of ultrasound transducers 18 reach the whole imaging region of the subject.

The reception circuit receives and amplifies the ultrasonic detection signal output from each ultrasound transducer 18. Since the distances between the respective ultrasound transducers 18 and an ultrasonic wave reflection source in the subject differ from each other, the times until a reflected wave reaches the respective ultrasound transducers 18 differ from each other. The reception circuit includes a delay circuit, and delays each detection signal by the amount corresponding to the difference (delay time) in the reaching time of the reflected wave in accordance with a reception delay pattern which is set on the basis of sound speed (hereinafter, referred to as assumed sound speed) or distribution of sound speed selected by controller 14.

Next, the reception circuit performs reception focus processing by matching and adding the detection signals to which the delay time is given. When different ultrasonic wave reflection sources exist at positions different from an ultrasonic wave reflection source X, since ultrasonic detection signals from the different ultrasonic wave reflection sources are different from each other in the reaching time, the phases of the ultrasonic detection signals from the different ultrasonic wave reflection sources are canceled each other out by the addition in the addition circuit. Accordingly, the reception signal from the ultrasonic wave reflection source X becomes largest, and comes into focus. With this reception focus processing, the focus of the ultrasonic echo is narrowed to generate a sound ray signal (hereinafter, referred to as an RF signal).

In the A/D converter, an analog RF signal which is output from the reception circuit is converted to a digital RF signal (hereinafter, referred to as RF data), and the RF data is output. The RF data includes phase information of a reception wave (carrier wave).

In the signal processor 22, after correction of attenuation depending on the distance in accordance with the depth of the reflection position of the ultrasonic wave is made for the RF data through STC (Sensitivity Time gain Control), an envelope detection processing is performed, and B-mode image data is generated and output.

The B-mode image data and the RF data for each set sound speed are input to the focus index calculator 26, and a focus index for each set sound speed necessary for obtaining the ambient sound speed value is calculated for each pixel of the B-mode image. If the focus index for a certain set sound speed is calculated, the set sound speed is changed and the focus index is calculated. That is, the focus indices are calculated and output for all set sound speeds. As the focus index, for example, contrast and sharpness of the image, or the period or amplitude of the ultrasonic detection signal in each pixel is used from the B-mode image data, and a beam width is used from the RF data.

The focus indices of all set sound speeds for each pixel of the B-mode image are input to the ambient sound speed profile generator 28. The focus indices input are plotted on a graph in which the horizontal axis represents the set sound speed and the vertical axis represents the focus index, and a set sound speed profile (hereinafter, referred to an ambient sound speed profile) is generated and output.

The ambient sound speed profile obtained for each pixel of the B-mode image is input to the ambient sound speed value determiner 30. The optimum sound speed value (hereinafter, referred to as an ambient sound speed value) for each pixel is determined on the basis of the input ambient sound speed profile and output. Here, the optimum sound speed value (ambient sound speed value) is a sound speed value at which contrast and sharpness of the image are highest, and a sound speed value at which the beam width is smallest, and is not necessarily consistent with an actual sound speed value (local sound speed value) in each pixel.

Alternatively, as a method which obtains an ambient sound speed value, for example, a method which decides an ambient sound speed value from the spatial frequency, dispersion, or the like in a scanning direction (for example, JP 8-317926 A) may be used.

The ambient sound speed value obtained for each pixel of the B-mode image is input to the sound speed image generator 32. In the sound speed image generator 32, an image in which values corresponding to the ambient sound speed values, for example, a given range of numerical values associated with a given range of sound speeds such that gradation expression is possible, are allocated to the respective pixels of the B-mode image (hereinafter, this image is referred to as a sound speed image) is generated and output as sound speed image data. Pseudo color imaging may be performed for a given range of numerical values capable of a gradation expression.

Furthermore, in a state where the ultrasound probe 16 remains stationary, a plurality of sound speed images may be generated, and the average value between the plurality of sound speed images in a time axis (frame) direction may be calculated, such that a measurement error-suppressed sound speed image in which measurement errors are suppressed may be obtained.

The sound speed image data is input to the first reliability image generator 34. The first reliability image generator 34 serves as a reliability information generator and a reliability image generator. In the first reliability image generator 34, reliability information is generated for each pixel of the sound speed image, and a reliability image is generated by imaging the reliability information and output as reliability image data. In regard to the reliability information, for example, the standard deviation of variations in the ambient sound speed value of each pixel of the sound speed image and a predetermined range of pixels (for example, 3×3 pixels) around each pixel may be obtained and defined as a value of a center pixel. The reliability information obtained for all pixels is imaged and output as reliability image (standard deviation image) data.

Alternatively, in regard to the reliability information, the standard deviation of variations in the ambient sound speed value of the corresponding pixel between a plurality of sound speed images of the same region of interest with different acquisition times may be obtained, imaged in the same manner as described above, and output as reliability image data. These may be combined, that is, the standard deviation of variations in the ambient sound speed value of a three-dimensional predetermined range of pixels with respect to the x axis, the y axis, and the time axis (frame) of an image may be obtained.

Even if the ambient sound speed in each pixel is constant, when there are mediums with different sound speeds between the ultrasound probe 16 and the region of interest, the ambient sound speed changes in the depth direction. Accordingly, in order to exclude this change from calculation of reliability, approximation may be made with a plane which changes in the depth direction in accordance with a liner expression or a quadratic expression, and the standard deviation may be obtained after subtracting the ambient sound speed value obtained by the approximation from the ambient sound speed value in each pixel.

Furthermore, when the ultrasound probe 16 is moved and a plurality of sound speed images are generated, the standard deviation of variations in the ambient sound speed value of the same pixel of interest between the sound speed images (frames) may be obtained.

The ambient sound speed profile obtained for each pixel of the B-mode image is input to the second reliability image generator 36. The second reliability image generator 36 serves as a reliability information generator and a reliability image generator. In the second reliability image generator 36, reliability information is generated on the basis of the shape of the input ambient sound speed profile or the sound speed image for each pixel of the B-mode image, the reliability information is imaged to generate a reliability image, and reliability image data is output. The reliability information generator and the reliability image generator are constituted by the first reliability image generator 34 and the second reliability image generator 36 separately or in combination.

Figure 2A:
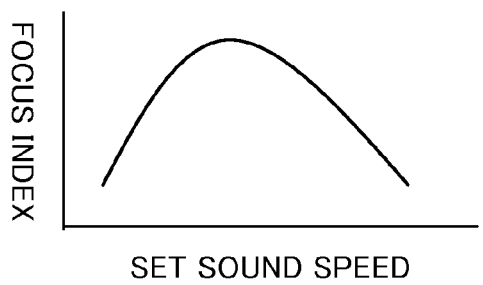
FIGS. 2A and 2B are graphs illustrating an example of a set sound speed profile.

The shape of the ambient sound speed profile will be described. When the reliability of the ambient sound speed value is high, for example, as illustrated in FIG. 2A, the focus index undergoes monomodal change in which the closer it is to the ambient sound speed value, the greater it becomes monotonously. The difference between the focus index at the ambient sound speed value and the focus index at the set sound speed value out of the ambient sound speed value becomes large. That is, contrast increases.

Figure 2B:
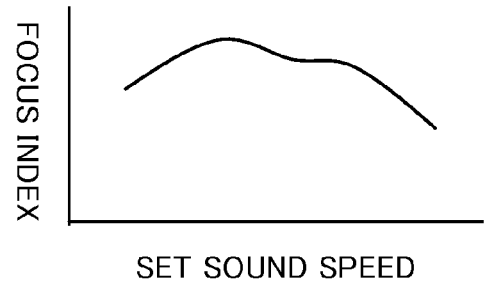

On the other hand, when the reliability of the ambient sound speed value is low, for example, as illustrated in FIG. 2B, the focus index may change intricately depending on the set sound speed, and may undergo bimodal or trimodal change. The difference between the focus index at the ambient sound speed value and the focus index at the set sound speed value out of the ambient sound speed value becomes small. That is, contrast decreases.

For this reason, the reliability information may be generated using distortion of the shape of the ambient sound speed profile, for example, using an order capable of reducing error in curve fitting, error with a result of quadratic curve fitting with the maximum value as an apex, dispersion (second moment) of the set sound speed value, and third moment of the set sound speed value.

Moreover, the reliability information may be generated using the contrast of the focus index, for example, using the difference between the maximum value and the minimum value of the focus index, the focus index expressed by the following Expression (1), and the average value of the derivative absolute values of the focus index.

Focus Index=Maximum Focus Index−(Focus Index[1400]+ Focus Index[1650])/2       (1)

Moreover, on the basis of the fact that the focus index depends on luminance of the B-mode image or frequency, the reliability information may be generated using a value obtained by normalizing the above-described error or contrast with the average value or the maximum value of the focus index.

The B-mode image data, the sound speed image data, and the reliability image data are input to the image processor 38. The image processor 38 has a DSC (Digital Scan Converter) function and an image processing function, such as edge detection, gap detection, overlay display of various kinds of image data (B-mode image data, sound speed image data and reliability image data), highlighting and mask processing. Display image data implemented with DSC and image processing is output from the image processor 38. In regard to the B-mode image data which is used in overlay display or the like, it is preferable to use data at the set sound speed at which the focus of the whole image is most excellent.

In the DSC function, since the B-mode image data, and the sound speed image data and the reliability image data generated based on the B-mode image data are based on a scan system different from a normal television signal scan system, conversion (raster conversion) to normal image data (for example, image data of a television signal scan system (NTSC system)) is performed so as to be displayable on the display unit 40 described below.

In the image processing function, for example, overlay images of various kinds of image data are generated, reliable pixels are highlighted, or less reliable pixels are masked and not displayed, whereby images which assist diagnosis by a physician are generated. For example, a measurement error image may be generated on the basis of measurement error information acquired from, of pixels of a reliability image, pixels of interest having reliability information equal to or less than a predetermined value which is considered as measurement error, and the measurement error image may be displayed on the sound speed image in an overlay manner.

For example, when edge detection processing or gap detection processing is performed on a sound speed image, that is, when a plurality of pixels are set within a two-dimensional section or three-dimensionally by including the time axis (frame) direction around a pixel of interest, and a set of pixels in which the difference in the ambient sound speed value between adjacent pixels is equal to or larger than a predetermined value is included (that is, when discontinuous point is included), by detecting the pixel of interest as measurement error, measurement error information may be acquired to generate a measurement error image as a reliability image, and the measurement error image may be displayed on the sound speed image in an overlay manner. At this time, approximation may be made with a plane which changes in the depth direction in accordance with a linear expression or a quadratic expression, and a discontinuous portion may be decided after subtracting the ambient sound speed value obtained by the approximation from the ambient sound speed value in each pixel and detected as measurement error.

The display image data is input to and displayed on the display unit 40. The display unit 40 is constituted by an FPD (Flat Panel Display) such as liquid crystal, plasma or organic EL (Electro Luminescence), or a CRT (Cathode Ray Tube). For the display unit 40, a display unit having a large display area and a large number of pixels may preferably be used such that a plurality of images can be displayed in parallel.

Information (for example, parameters representing the depth of the reflection position of the ultrasonic wave, the density of the scan lines, and the visual field width) relating to the RF data and a frame rate is input to the RF data recorder/reproducer 42, and is recorded in an internal cine memory. The RF data recorder/reproducer 42 has two operation modes of a cine memory recording mode and a cine memory reproduction mode. At the time of normal observation (live mode), the RF data recorder/reproducer 42 operates in the cine memory recording mode to record the RF data.

The cine memory reproduction mode is a mode in which an ultrasound diagnostic image is displayed, analyzed and measured on the basis of the RF data stored in the cine memory. In the cine memory reproduction mode, the RF data stored in the cine memory is output to the signal processor 22 in accordance with operation by an operator, and the operator can view the B-mode image, the sound speed image and the reliability image based on the RF data recorded in the RF data recorder/reproducer 42.

Next, the operation of the ultrasound image generating device 10 according to the invention which realizes the ultrasound image generating method according to the invention will be described.

Figure 3:
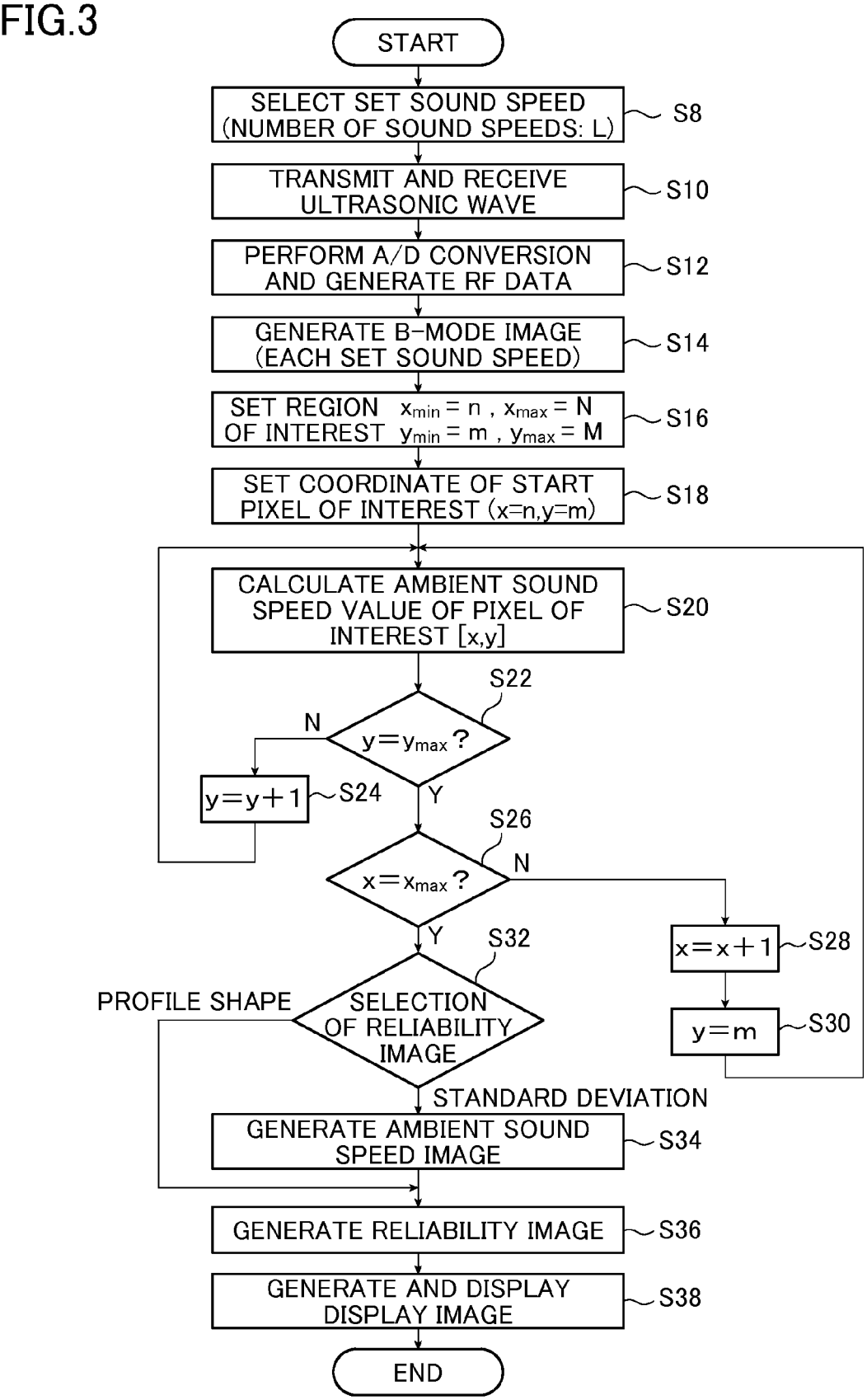
FIG. 3 is a flowchart illustrating an example of the flow of processing of the ultrasound image generating method according to the first embodiment of the invention.
Figure 4:
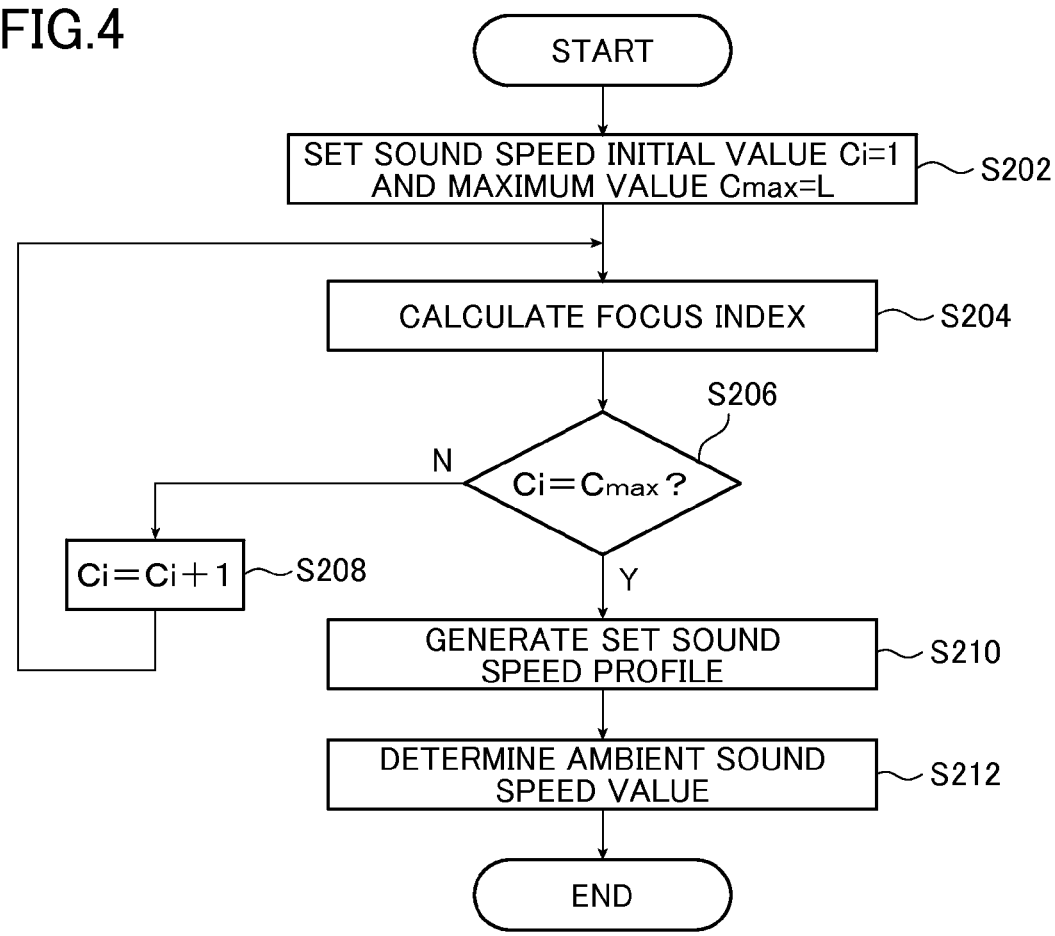
FIG. 4 is a flowchart illustrating an example of the flow of processing for determining a sound speed value.

FIGS. 3 and 4 are flowcharts illustrating an example of the flow of processing of the ultrasound image generating method according to the invention.

First, a plurality of set sound speeds for obtaining the ambient sound speed value are selected by the controller 14 and are set for the transmitter/receiver 20 (Step S8). In regard to the set sound speed, a plurality of sound speeds are selected and set from a range of sound speed in a human body (about 1400 m/s to 1650 m/s). The number (L) of sound speeds to be selected may be set such that, when plotting them on a graph which has the horizontal axis representing the set sound speed and the vertical axis representing the focus index, a graph such as in FIGS. 2A and 2B is drawn. Alternatively, the operator may set the set sound speeds.

Subsequently, the operator brings the ultrasound probe 16 into contact with the subject to perform transmission and reception of an ultrasonic wave, and an ultrasonic detection signal is output from the ultrasound probe 16 (Step S10). The ultrasonic detection signal is input to the transmitter/receiver 20, subjected to the reception focus processing or transmission and reception focus processing for each set sound speed on the basis of the reception delay patterns corresponding to the selected set sound speeds, A/D (Analog/Digital) converted, and output as RF data for each set sound speed (Step S12).

Figure 5:
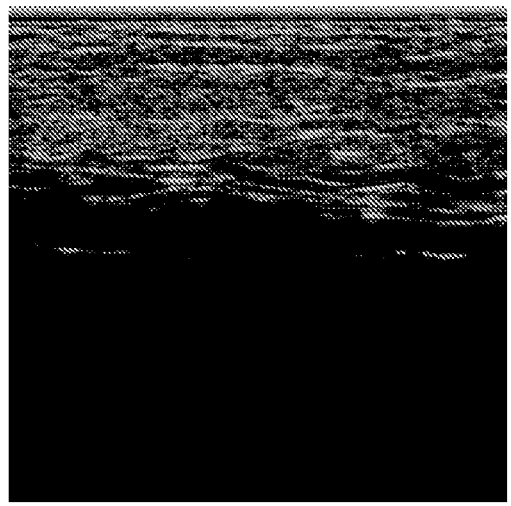
FIG. 5 is an explanatory view illustrating an example of a B-mode image.

The RF data for each set sound speed is input to the signal processor 22, subjected to correction of attenuation depending on the distance through the STC in accordance with the depth of the reflection position of the ultrasonic wave, and subjected to the envelope detection processing, and B-mode image data of a B-mode image such as shown in FIG. 5 is generated for each set sound speed and output (Step S14).

Figure 6:
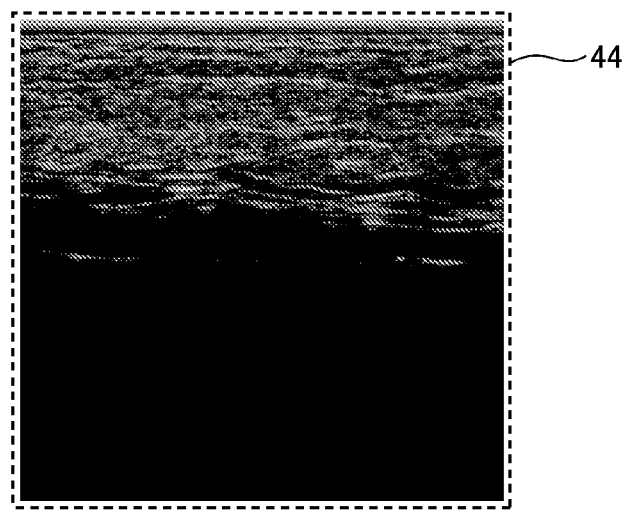
FIG. 6 is an explanatory view illustrating an example of setting of a region of interest.

The B-mode image data and the RF data for all the set sound speeds are input to the ambient sound speed value calculator 24. In the ambient sound speed value calculator 24, a region of the B-mode image where a sound speed image or a reliability image is desired to be obtained is designated as a region of interest (Step S16). In regard to the region of interest, for example, as illustrated in FIG. 6, the whole B-mode image may be set automatically as a region of interest 44 at the initial setting, or a part of the B-mode image may be set automatically as a region of interest. The operator may operate the operating unit 12 to set a part of the B-mode image as a region of interest. The region of interest is designated by, for example, start point coordinates [$x_{min}$, $y_{min}$] and end point coordinates [$x_{max}$, $y_{max}$]. In the flowchart of FIG. 3, as an example, x is set in a range of n to N and y is set in a range of m to M.

If the region of interest is set, a start pixel of interest (for example, x=n, y=m) for starting calculation of the ambient sound speed value is set (Step S18), and calculation of the ambient sound speed value of the pixel of interest is performed (Step S20).

Here, the details of the calculation of the ambient sound speed value of the pixel of interest will be described on the basis of a flowchart of FIG. 4.

First, the number of the sound speeds (number of the set sound speeds) selected for obtaining the ambient sound speed value set in Step S8 is set to have an initial value $c_i$=1 and a maximum value $c_{max}$=L (Step S202).

Next, the focus index of the set sound speed $C_i$ is calculated and output (Step S204). As the focus index value, for example, the values of contrast and sharpness of the B-mode image data are calculated and output. A predetermined index may be calculated from the beam width of the RF data of the pixel of interest and output as a focus index.

If the calculation of the focus index for $C_i$=1 (initial value) ends, the values of $C_i$ and $C_{max}$ (maximum value) are compared with each other (Step S206). When the value of $C_i$ is less than $C_{max}$ ("N" in Step S206), 1 is added to $C_i$ (Step S208), and the process is returned to the calculation of the focus index in Step S204. The calculation (Step S204) of the focus index is repeated until achieving $C_i$=$C_{max}$, and the focus index is calculated and output for all the set sound speeds of the pixel of interest.

The focus indices for all the set sound speeds of the pixel of interest are input to the ambient sound speed profile generator 28, and are plotted on a graph which has the horizontal axis representing the set sound speed and the vertical axis representing the focus index. Thus, an ambient sound speed profile is generated and output (Step S210).

The ambient sound speed profile is input to the ambient sound speed value determiner 30, and, for example, in the case where the ambient sound speed profile is one as shown in FIG. 2A, the set sound speed value with the maximum value of the focus index is determined as the ambient sound speed value and output (Step S212).

If the calculation of the ambient sound speed value of the pixel of interest ends, that is, if Step S20 ends, the value of the y coordinate of the pixel of interest is compared with $y_{max}$ (Step S22). When the value of y is less than $y_{max}$ ("N" in Step S22), 1 is added to y (Step S24), and the process is returned to the calculation of the ambient sound speed value of the pixel of interest in Step S20. The calculation of the ambient sound speed value of the pixel of interest (Step S20) is repeated until achieving y=$y_{max}$.

Upon achieving y=$y_{max}$ ("Y" in Step S22), the value of the x coordinate of the pixel of interest is compared with $x_{max}$ (Step S26). When the value of x is less than $x_{max}$ ("N" in Step S26), 1 is added to x (Step S28), the value of the y coordinate is set to $y_{min}$ (y=m) (Step S30), and the process is returned to the calculation of the ambient sound speed value of the pixel of interest in Step S20. That is, when the y coordinate direction is referred to as a line, if the ambient sound speed value of the first line with the x coordinate of n is calculated, the x coordinate is incremented by 1 (n+1), and the ambient sound speed value of the second line is calculated. The calculation of the ambient sound speed value of the pixel of interest (Step S20) is repeated until the ambient sound speed value is calculated for the whole region of interest (until achieving x=$x_{max}$ (x=N), y=$y_{max}$ (y=M)).

If the calculation of the ambient sound speed value for the whole region of interest ends, the ambient sound speed value is input to the sound speed image generator 32, and the ambient sound speed profile is input to the second reliability image generator 36.

Here, selection information relating to a reliability image is set in advance, or the operating unit 12 is operated by the operator and a reliability image is selected by the controller 14 (Step S32). When a standard deviation image is selected as a reliability image ("standard deviation" in Step S32), in the sound speed image generator 32, the ambient sound speed value corresponding to each pixel of the B-mode image is allocated, and the ambient sound speed image is generated and output as ambient sound speed image data (Step S34).

The ambient sound speed image data is input to the first reliability image generator 34 and the image processor 38. In the first reliability image generator 34, reliability information for each pixel of the sound speed image is generated, and the reliability information is imaged to generate a reliability image and output as reliability image data (Step S36).

On the other hand, when an ambient sound speed profile shape image is selected as a reliability image in Step S32 ("profile shape" in Step S32), reliability information is generated for each pixel of the B-mode image on the basis of the ambient sound speed profile shape for each pixel of the B-mode image input to the second reliability image generator 36 without using the ambient sound speed image, and the reliability information is imaged to generate a reliability image and output as reliability image data (Step S36).

The B-mode image data, the ambient sound speed image data, and the reliability image data are input to the image processor 38. In the image processor 38, conversion to normal image data, overlay display, highlighting, mask processing, and the like are performed for various kinds of input image data to generate display image data, and the display image data is output to and displayed on the display unit 40 (Step S38). Edge detection, gap detection, and the like may be performed for various kinds of image data to acquire measurement error information to generate a measurement error image.

Figure 7:
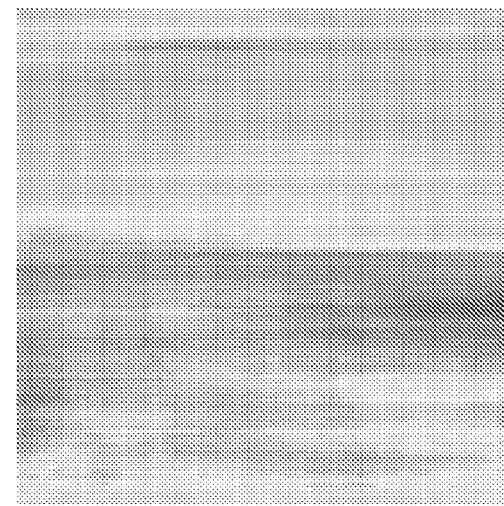
FIG. 7 is an explanatory view illustrating an example of a sound speed image obtained by imaging an ambient sound speed value.
Figure 8:
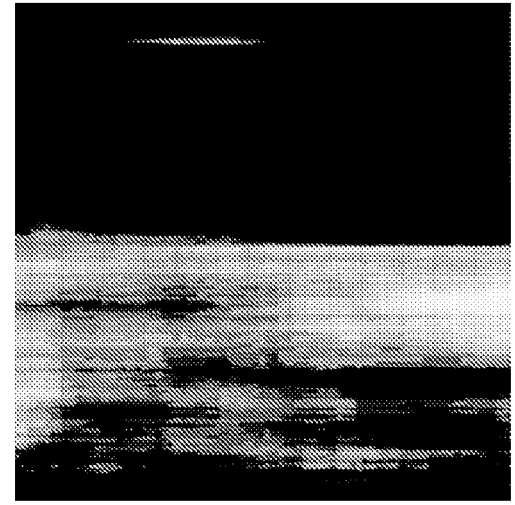
FIG. 8 is an explanatory view illustrating an example of a reliability image obtained by imaging reliability of sound speed.
Figure 9:
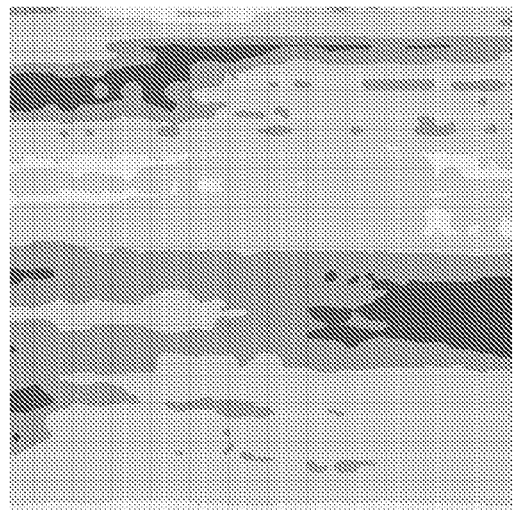
FIG. 9 is an explanatory view illustrating an example of a reliability image obtained by imaging reliability of a set sound speed profile shape.

An example of display image data which is displayed on the display unit 40 will be described. For example, the B-mode image illustrated in FIG. 5 or the ambient sound speed image illustrated in FIG. 7, and the reliability image (standard deviation image) illustrated in FIG. 8 or the reliability image (sound speed profile shape) illustrated in FIG. 9 can be displayed in parallel.

Figure 10:
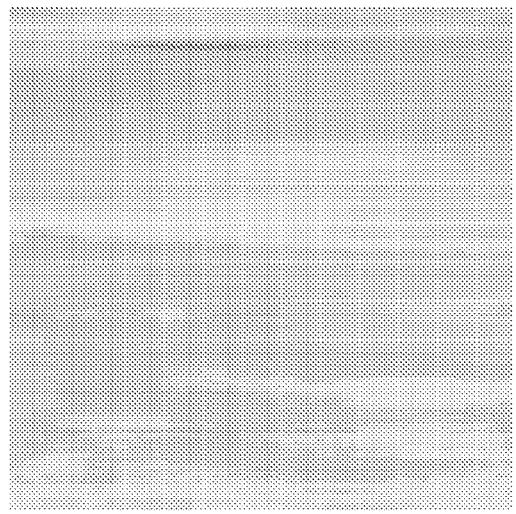
FIG. 10 is an explanatory view illustrating an example of display of a sound speed image.
Figure 11:
FIG. 11 is an explanatory view illustrating another example of display of a sound speed image.

Also, for example, as illustrated in FIG. 10, the color (luminance, hue, color saturation) of the ambient sound speed image may be modulated and displayed alone or in parallel, or the color of the reliability image or the measurement error image may be modulated instead of the ambient sound speed image and displayed alone or in parallel. Furthermore, as illustrated in FIG. 11, the B-mode image of FIG. 5 and the ambient sound speed image of FIG. 7 may be displayed in an overlay manner.

The display of the B-mode image or the ambient sound speed image may be limitedly performed such that less reliable pixels or pixels with measurement errors are not displayed, or only reliable pixels are displayed. For example, as illustrated in FIG. 12, the ambient sound speed image of FIG. 7 can be displayed in a state of being masked with the reliability image of FIG. 8.

In addition to the above, for example, as illustrated in FIG. 13, the B-mode image illustrated in FIG. 5 and an image in which the color of the ambient sound speed image illustrated in FIG. 10 is modulated may be displayed in an overlay manner, or as illustrated in FIG. 14, the B-mode image illustrated in FIG. 5 and an image in which the ambient sound speed image illustrated in FIG. 12 is masked with the reliability image may be displayed in an overlay manner.

The operator may arbitrarily switch the display mode of the foregoing various display images through the operating unit 12.

As described above, it is possible to provide various ambient sound speed images and reliability images such that a lesion in the subject is more easily detected, without using a configuration in which a dedicated ultrasonic wave for measuring the ambient sound speed value is transmitted and received.

Figure 15:
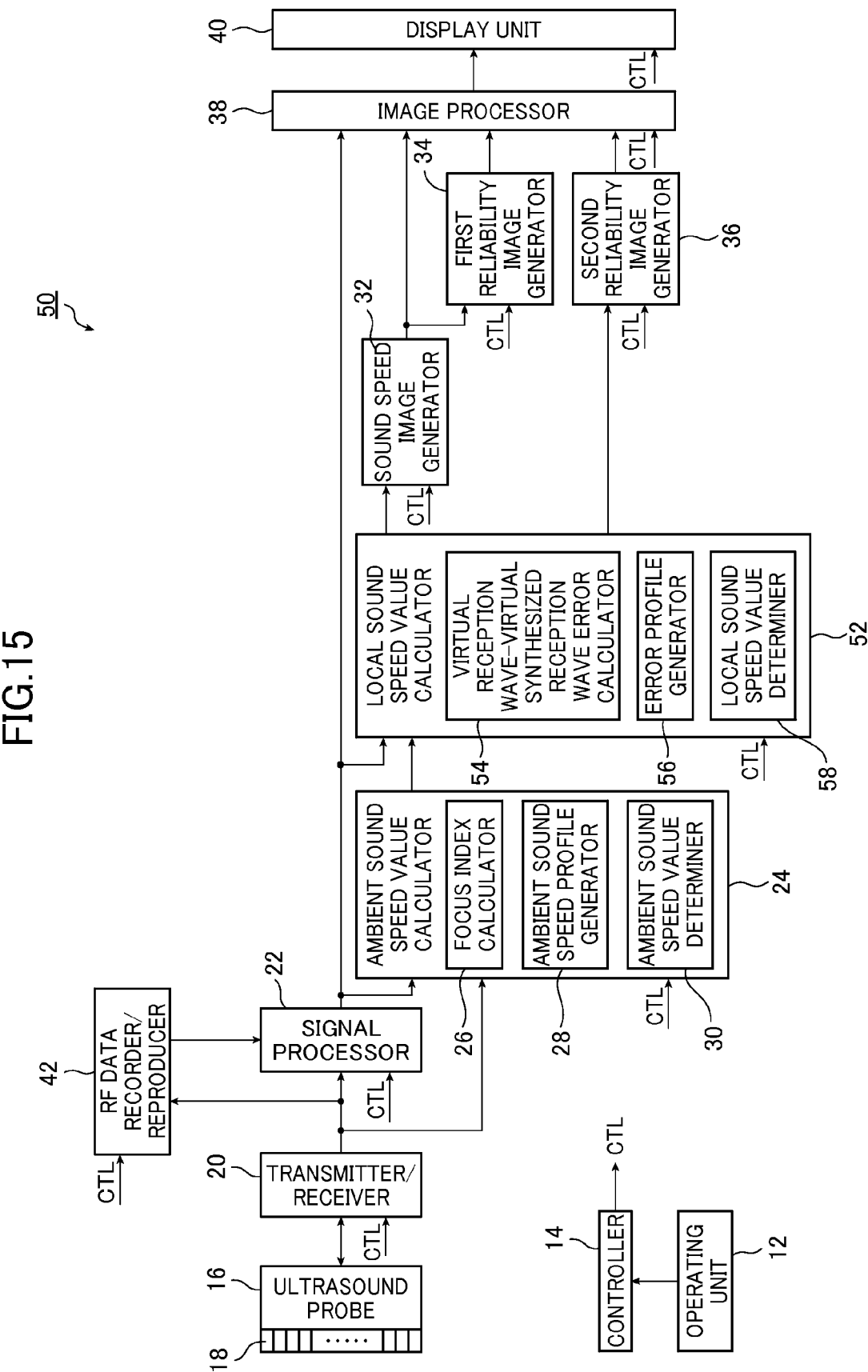
FIG. 15 is a block diagram illustrating an example of the configuration of an ultrasound image generating device according to a second embodiment of the invention which executes an ultrasound image generating method according to the invention.

Next, as a second embodiment, a case where the local sound speed value is used instead of the ambient sound speed value will be described. FIG. 15 is a block diagram illustrating the configuration of an ultrasound image generating device 50 according to the second embodiment which is different from the above-mentioned first embodiment, of the invention.

The ultrasound image generating device 50 basically has the same configuration as the ultrasound image generating device 10 according to the first embodiment of the invention illustrated in FIG. 1, except that a local sound speed value is further obtained from an ambient sound speed value, and a sound speed image and a reliability image are generated using the local sound speed value. Accordingly, the same constituent elements are represented by the same reference numerals, and detailed description thereof will not be repeated.

In the ultrasound image generating device 50 illustrated in FIG. 15, an ambient sound speed value of each pixel which is an output of the ambient sound speed value calculator 24 is input to a local sound speed value calculator 52, a local sound speed value which is output from the local sound speed value calculator 52 is input to the sound speed image generator 32 and the second reliability image generator 36, and an error profile which is also output from the local sound speed value calculator 52 is input to the second reliability image generator 36.

The local sound speed value calculator 52 includes a virtual reception wave-virtual synthesized reception wave error calculator 54, an error profile generator 56 and a local sound speed value determiner 58.

B-mode image data and the ambient sound speed value are input to the virtual reception wave-virtual synthesized reception wave error calculator 54, and error between a virtual reception wave and a virtual synthesized reception wave is calculated for each assumed local sound speed necessary for obtaining the local sound speed value for each pixel of the B-mode image. That is, the error between the virtual reception wave and the virtual synthesized reception wave is calculated and output for all the assumed local sound speeds.

The errors between the virtual reception wave and the virtual synthesized reception wave for all the assumed local sound speeds for each pixel of the B-mode image are input to the error profile generator 56. The input errors between the virtual reception wave and the virtual synthesized reception wave are plotted on a graph which has the horizontal axis representing the assumed local sound speed and the vertical axis representing the error between the virtual reception wave and the virtual synthesized reception wave to generate an error profile, and the error profile is output.

The error profile obtained for each pixel of the B-mode image is input to the local sound speed value determiner 58. The local sound speed value for each pixel is determined on the basis of the input error profile and output.

Here, processing for calculating the local sound speed value will be described.

Figure 16:
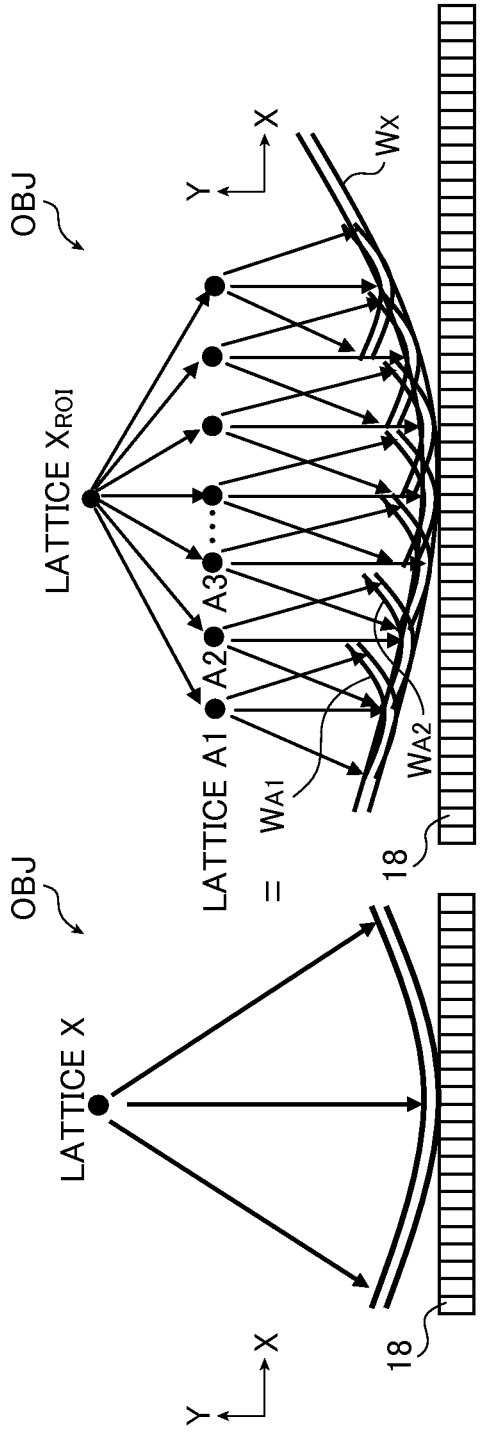
FIGS. 16A and 16B are explanatory views schematically illustrating processing for calculating a local sound speed value according to the invention.

FIG. 16A is a diagram schematically illustrating processing for calculating the local sound speed value.

As illustrated in FIG. 16B, it is assumed that a lattice point representing a region of interest ROI in a subject OBJ is referred to as $X_{ROI}$, lattice points which are arranged at regular intervals in the XY direction at positions shallower than the lattice point $X_{ROI}$ (close to the ultrasound transducer 18) are referred to as A1, A2, . . . , and at least the sound speed between the lattice point $X_{ROI}$ and each of the lattice points A1, A2, . . . is constant.

In this example, it is assumed that (T and the delay time ΔT) of the reception waves ($W_{A1}, W_{A2}, \ldots$) from the lattice points A1, A2, . . . are known, and the local sound speed value at the lattice point $X_{ROI}$ is obtained from the positional relationship between the lattice point $X_{ROI}$ and the lattice points A1, A2, . . . . Specifically, On the basis of the Huygens principle, the fact that a reception wave $W_X$ from the lattice point $X_{ROI}$ is consistent with a reception wave $W_{SUM}$ obtained by virtually synthesizing the reception waves from the lattice points A1, A2, . . . is used.

The range and the number of the lattice points A1, A2, . . . which are used for calculation for obtaining the local sound speed value at the lattice point $X_{ROI}$ are determined in advance. If the range of the lattice points which are used for calculating the local sound speed value is wide, the error of the local sound speed value increases, and if the range is narrow, the error with the virtual reception wave increases. For this reason, the range of the lattice points is determined taking this fact into consideration.

The interval between the lattice points A1, A2, . . . in the X direction is determined taking into consideration the resolution and the processing time. As an example, the interval between the lattice points A1, A2, . . . in the X direction is 1 mm to 1 cm.

If the interval between the lattice points A1, A2, . . . in the Y direction is narrow, error in error calculation increases, and if the interval is wide, error of the local sound speed value increases. The interval between the lattice points A1, A2, . . . in the Y direction is determined on the basis of the setting of the image resolution of the ultrasound image. As an example, the interval between the lattice points A1, A2, . . . in the Y direction is 1 cm.

When the interval between the lattice points A1, A2, . . . is wide, since the calculation of the synthesized wave becomes difficult, fine lattice points may be generated by interpolation.

Since the operation of the ultrasound image generating device 50 of the second embodiment is about the same as the ultrasound image generating device 10 of the first embodiment, description thereof will not be repeated, and only different portions will be described with reference to the flowchart shown in FIG. 17.

Figure 17:
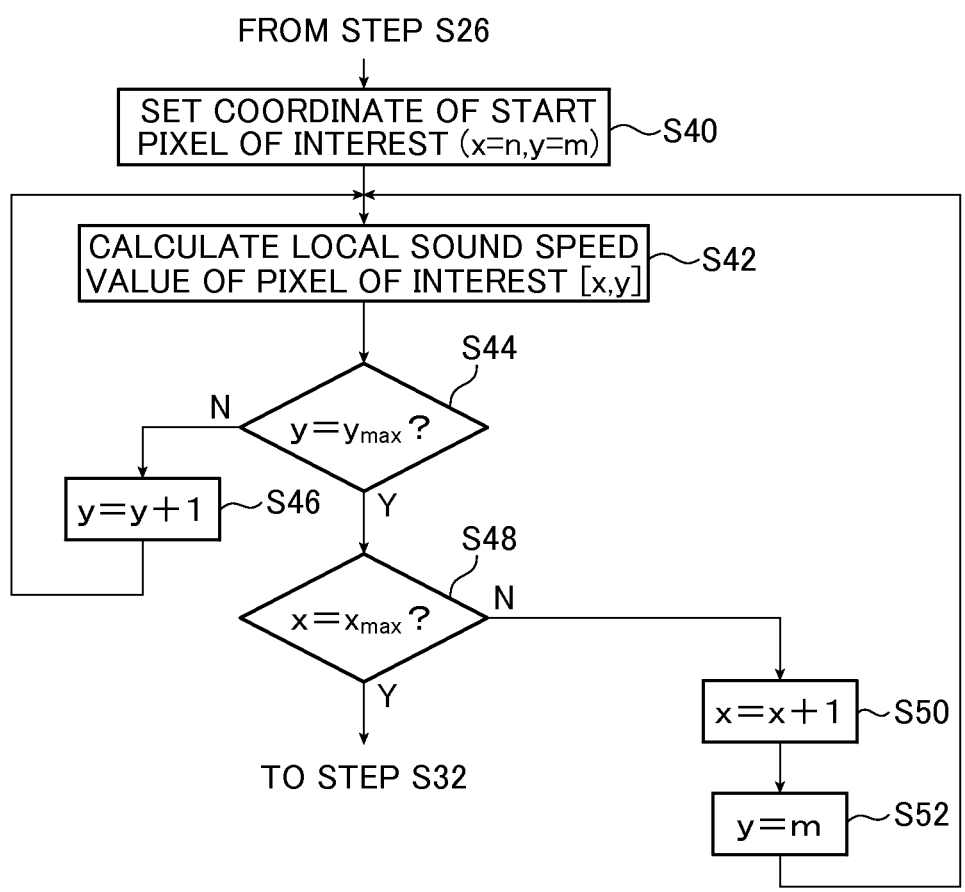
FIG. 17 is a flowchart illustrating an example of the flow of processing of the ultrasound image generating method according to the second embodiment of the invention.

FIG. 17 is a flowchart which is additionally provided between Step S26 and Step S32 of FIG. 3.

Up to Step S26, the ambient sound speed value is obtained for all pixels of the region of interest.

Subsequently, a start pixel of interest (for example, x=n, y=m) for starting calculation of the local sound speed value is set (Step S40), and calculation of the local sound speed value of the pixel of interest is performed (Step S42).

The details of the calculation of the local sound speed value of the pixel of interest will be described on the basis of the flowchart of FIG. 18.

First, the waveform of the virtual reception wave $W_X$ when the lattice point $X_{ROI}$ is defined as a reflection point is calculated on the basis of the ambient sound speed value at the lattice point $X_{ROI}$ (Step S302).

Next, the initial value of an assumed sound speed at the lattice point $X_{ROI}$ is set (Step S304). Then, the assumed sound speed is changed by one step (Step S306), and the virtual synthesized reception wave $W_{SUM}$ is calculated (Step S308). If it is assumed that the local sound speed value at the lattice point $X_{ROI}$ is V, the time until an ultrasonic wave which propagates from the lattice point $X_{ROI}$ reaches the lattice points A1, A2, . . . becomes $X_{ROI}$A1/v, $X_{ROI}$A2/V, . . . . Here, $X_{ROI}$A1, $X_{ROI}$A2, . . . are the distances between the lattice points A1, A2, . . . and the lattice point $X_{ROI}$, respectively. Since the ambient sound speed values at the lattice points A1, A2, . . . are known through the process up to Step S26 of FIG. 3, the reception waves from the lattice points A1, A2, . . . can be obtained in advance. Accordingly, the reflected waves (ultrasonic echo) radiated from the lattice points A1, A2, . . . with the respective delay $X_{ROI}$A1/V, $X_{ROI}$A2/V, . . . are synthesized, thereby obtaining the virtual synthesized reception wave $W_{SUM}$.

Practically, since the above-described processing is performed on element data (RF signal), the time (T1, T2, . . . , respectively) taken to reach the lattice points A1, A2, . . . from the lattice point $X_{ROI}$ is expressed by the following Expression (2). In Expression (2), $X_{A1}, X_{A2}, \ldots$ are the distances between the lattice points A1, A2, . . . and the lattice point X in the scan direction (X direction), respectively, and Δt is the time interval of Y-direction between the lattice points.

[Equation 1]

$$T1 = \sqrt{(X_{A1}/V)^2 + (\Delta t/2)^2},$$

$$T2 = \sqrt{(X_{A2}/V)^2 + (\Delta t/2)^2},$$

$$T3 = \ldots \qquad (2)$$

The reception waves from the lattice points A1, A2, . . . with the delay obtained by adding the time (Δt/2) taken to reach the lattice point $X_{ROI}$ from a lattice point An of the same sound ray as the lattice point $X_{ROI}$ to T1, T2, . . . above are synthesized, thereby obtaining the virtual synthesized reception wave $W_{SUM}$.

When the lattice points are set at regular time intervals (Δt) in the Y direction, the interval on a space is not necessarily a regular interval. Accordingly, when calculating the time until an ultrasonic wave reaches each lattice point, instead of Δt/2, corrected Δt/2 may be used in Expression (2). The corrected Δt/2 is a value which is obtained by adding or subtracting to or from Δt/2 a value obtained by dividing the difference in the depth (the distance in the Y direction) between A1, A2, . . . and the lattice point An of the same sound ray as the lattice point $X_{ROI}$ by V. The depth of each of the lattice points A1, A2, . . . is obtained on the basis of the fact that a local sound speed value at a shallower lattice point than the lattice points A1, A2, . . . is known.

The calculation of the virtual synthesized reception wave $W_{SUM}$ is performed by superimposing default pulse waves ($W_{A1}, W_{A2}, \ldots$) practically radiated from the lattice points A1, A2, . . . with the delay $X_{ROI}$A1/v, $X_{ROI}$A2/V, . . . .

Next, the error between the virtual reception wave $W_X$ and the virtual synthesized reception wave $W_{SUM}$ is calculated (Step S310). The error between the virtual reception wave $W_X$ and the virtual synthesized reception wave $W_{SUM}$ is calculated by a method which takes a cross-correlation, a method which multiplies the virtual reception wave $W_X$ and the delay obtained from the virtual synthesized reception wave $W_{SUM}$ together and performs phase matching and adding, or a method which conversely multiplies the virtual synthesized reception wave $W_{SUM}$ and the delay obtained from the virtual reception wave $W_X$ together and performs phase matching and adding. In order to obtain the delay from the virtual reception wave $W_X$, it should suffice that the lattice point $X_{ROI}$ is defined as a reflection point, and the time until an ultrasonic wave propagating at the sound speed V reaches each element is defined as a delay. In order to obtain the delay from the virtual synthesized reception wave $W_{SUM}$, an equiphase line may be extracted from the phase difference between the synthesized reception waves from adjacent elements and the equiphase line may be defined as a delay, or the phase difference at the maximum (peak) position of the synthesized reception wave of each element may be simply defined as a delay. Moreover, a cross-correlated peak position of the synthesized reception waves from the respective elements may be defined as a delay. The error at the time of phase matching and adding is obtained by a method which defines as the peak to peak of a waveform after phase matching and adding, or a method which defines as the maximum value of amplitude after envelope detection.

Next, Steps S306 to S310 are repeated, and if the calculation with the values of all the assumed sound speeds ends ("Y" in Step S312), the local sound speed value at the lattice point $X_{ROI}$ is decided (Step S314). When the Huygens principle is strictly applied, the waveform of the virtual synthesized reception wave $W_{SUM}$ obtained in the above Step S308 is identical to the waveform of the virtual reception wave (reflected wave) $W_X$ of when it is assumed that the local sound speed value at the lattice point $X_{ROI}$ is V. In Step S314, the value of assumed sound speed at which the difference between the virtual reception wave $W_X$ and the virtual synthesized reception wave $W_{SUM}$ is minimal is decided as the local sound speed value at the lattice point $X_{ROI}$.

Instead of the above-described methods (calculation of the virtual synthesized reception waveform, calculation of the error with the virtual reception waveform, and sound speed decision), a table which has the ambient sound speed value of the lattice point $X_{ROI}$ and the ambient sound speed values of the lattice points A1, A2, . . . as input, and the sound speed value at the lattice point $X_{ROI}$ as output may be used.

The decision of the local sound speed value may be made multiple times using lattice points at different intervals or in different ranges.

If the calculation of the local sound speed value of the pixel of interest ends, that is, if Step S42 ends, the value of the y coordinate of the pixel of interest is compared with $y_{max}$ (Step S44). When the value of y is less than $y_{max}$ ("N" in Step S44), 1 is added to y (Step S46), and the process is returned to the calculation of the local sound speed value of the pixel of interest in Step S42. The calculation of the local sound speed value of the pixel of interest (Step S42) is repeated until achieving $y=y_{max}$.

If $y=y_{max}$ ("Y" in Step S44), the value of the x coordinate of the pixel of interest is compared with $x_{max}$ (Step S48). When the value of x is less than $x_{max}$ ("N" in Step S48), 1 is added to x (Step S50), the value of the y coordinate is set to $y_{min}$ (y=m) (Step S52), and the process is returned to the calculation of the local sound speed value of the pixel of interest in Step S42. That is, when the y coordinate direction is referred to as a line, if the local sound speed value of the first line with the x coordinate of n is calculated, the x coordinate is incremented by 1 (n+1), and the local sound speed value of the second line is calculated. The calculation of the local sound speed value of the pixel of interest (Step S42) is repeated until the local sound speed value is calculated for the whole region of interest (until achieving $x=x_{max}$ (x=N), $y=y_{max}$ (y=m)).

If the calculation of the local sound speed value for the whole region of interest ends, similarly to the process from Step S32 onward of the first embodiment, local sound speed image data and reliability image data are generated and displayed on the display unit 40.

As in the first embodiment, display image data which is displayed on the display unit 40 may be various types of display image data.

In this way, even when not only the ambient sound speed value but also the local sound speed value is used, it is possible to provide a local sound speed image and a reliability image such that a lesion in a subject is more easily detected, without using a configuration in which a dedicated ultrasonic wave for measuring a local sound speed value is transmitted and received.

Although in each embodiment, the B-mode image is generated and a pixel of the B-mode image is defined as a pixel of interest, the B-mode image may not be generated, the region of interest may be divided into a plurality of pixels on the basis of RF data, and the sound speed image may be generated with the plurality of pixels as pixels of interest.

Although in each embodiment, the ambient sound speed value or the local sound speed value is allocated to each pixel of the B-mode image to generate the sound speed image, the invention is not limited thereto, and the pixels of the sound speed image may not correspond to the pixels of the B-mode image on a one-to-one basis. For example, four pixels of the B-mode image may correspond to one pixel of the sound speed image.

Although in each embodiment, the operation at the time of the normal observation (live mode) has been described, the B-mode image, the sound speed image and the reliability image may be generated on the basis of RF data recorded in the RF data recorder/reproducer 42.

The invention may be constituted as an ultrasound image generating program which causes a computer to execute each step of the above-described ultrasound image generating method or an ultrasound image generating program which causes a computer to function as means for executing each step of the ultrasound image generating method or to function as means constituting the above-described ultrasound image generating device.

The invention may be constituted as a computer readable medium or a computer readable memory on which the above-described ultrasound image generating program is recorded.

Although the ultrasound image generating device, the ultrasound image generating method and the program according to the invention have been described in detail, the invention is not limited to the foregoing embodiments, and it is needless to say that various improvements and modifications are possible without departing from the gist of the invention.

DESCRIPTION OF SYMBOLS 10, 50 ULTRASOUND IMAGE GENERATING DEVICE
12 OPERATING UNIT
14 CONTROLLER
16 ULTRASOUND PROBE
18 ULTRASOUND TRANSDUCER
20 TRANSMITTER/RECEIVER
22 SIGNAL PROCESSOR
24 AMBIENT SOUND SPEED VALUE CALCULATOR
26 FOCUS INDEX CALCULATOR

28 AMBIENT SOUND SPEED PROFILE GENERATOR
30 AMBIENT SOUND SPEED VALUE DETERMINER
32 SOUND SPEED IMAGE GENERATOR
34 FIRST RELIABILITY IMAGE GENERATOR
36 SECOND RELIABILITY IMAGE GENERATOR
38 IMAGE PROCESSOR
40 DISPLAY UNIT
42 RF DATA RECORDER/REPRODUCER
44 REGION OF INTEREST
52 LOCAL SOUND SPEED VALUE CALCULATOR
54 VIRTUAL RECEPTION WAVE-VIRTUAL SYNTHESIZED RECEPTION WAVE CALCULATOR
56 ERROR PROFILE GENERATOR
58 LOCAL SOUND SPEED VALUE DETERMINER

What is claimed is:

1. An ultrasound image generating device which has an ultrasound probe which transmits an ultrasonic wave toward a subject, receives a reflected wave and outputs an ultrasonic detection signal, and which generates a morphological image representing a shape, the ultrasound image generating device further comprising:
a computer, wherein the computer comprises:
a sound speed value calculating processor which calculates a sound speed value in a region of interest of the morphological image;
a sound speed image generating processor which generates a sound speed image on the basis of the sound speed value of the region of interest;
a reliability information generating processor which generates reliability information of the sound speed value using the sound speed value of each of pixels of the sound speed image;
a reliability image generating processor which generates a reliability image on the basis of the reliability information;
an image processor which generates a display image from at least one of the morphological image, the sound speed image, or the reliability image; and
a display which displays the display image,
wherein the reliability information is information obtained from each of pixels of the sound speed image and a predetermined range of pixels including 3×3 pixels around each of the pixels, or measurement error information acquired when a discontinuous point is detected by edge detection processing or gap detection processing on the sound speed image,
the sound speed value calculating processor has an ambient sound speed value calculating processor which calculates an ambient sound speed value, and a local sound speed value calculating processor which calculates a local sound speed value on the basis of the ambient sound speed value, and
the sound speed value is the local sound speed value, and the sound speed image is a local sound speed image.

2. The ultrasound image generating device according to claim 1,
wherein the reliability information generating processor is adapted to generate the reliability information for each region corresponding to the region of interest of the sound speed image.

3. The ultrasound image generating device according to claim 1,
wherein the morphological image, and the sound speed image or the reliability image are displayed on the display in an overlay manner.

4. An ultrasound image generating device which has an ultrasound probe which transmits an ultrasonic wave toward a subject, receives a reflected wave and outputs an ultrasonic detection signal, and which generates a morphological image representing a shape, the ultrasound image generating device further comprising:
a computer, wherein the computer comprises:
a sound speed value calculating processor which calculates a sound speed value in a region of interest of the morphological image;
a sound speed image generating processor which generates a sound speed image on the basis of the sound speed value of the region of interest;
a reliability information generating processor which generates reliability information of the sound speed value using the sound speed value of each of pixels of the sound speed image;
a reliability image generating processor which generates a reliability image on the basis of the reliability information;
an image processor which generates a display image from at least one of the morphological image, the sound speed image, or the reliability image;
a display which displays the display image; and
a sound speed image generating processor,
wherein the sound speed value calculating processor is adapted to obtain a focus index value of each of pixels of the morphological image for each of set sound speeds, or obtain an error of a virtual reception wave and a virtual synthesized reception wave in each of pixels for each of assumed local sound speeds from each of the pixels and a predetermined range of pixels around the each of the pixels,
the reliability information generating processor is adapted to generate reliability information on the basis of the focus index value for each of the set sound speeds or the error for each of the assumed local sound speeds,
the sound speed value calculating processor is adapted further to calculate an ambient sound speed value or a local sound speed value in a region of interest of the morphological image on the basis of the focus index value for each of the set sound speeds and the error for each of the assumed local sound speeds,
the sound speed image generating processor is adapted to generate a sound speed image on the basis of the ambient sound speed value or the local sound speed value corresponding to the region of interest, and
the reliability information generating processor is adapted further to generate the reliability information for each region corresponding to the region of interest of the sound speed image.

5. An ultrasound image generating device which has an ultrasound probe which transmits an ultrasonic wave toward a subject, receives a reflected wave and outputs an ultrasonic detection signal, and which generates a morphological image representing a shape, the ultrasound image generating device further comprising:
a computer, wherein the computer comprises:
a sound speed value calculating processor which calculates a sound speed value in a region of interest of the morphological image;
a sound speed image generating processor which generates a sound speed image on the basis of the sound speed value of the region of interest;

a reliability information generating processor which generates reliability information of the sound speed value using the sound speed value of each of pixels of the sound speed image;

a reliability image generating processor which generates a reliability image on the basis of the reliability information;

an image processor which generates a display image from at least one of the morphological image, the sound speed image, or the reliability image; and a display which displays the display image, wherein the reliability information is information obtained from each of pixels of the sound speed image and a predetermined range of pixels including 3×3 pixels around each of the pixels, or measurement error information acquired when a discontinuous point is detected by edge detection processing or gap detection processing on the sound speed image, and display is performed in a state where pixels having the reliability information lower than a predetermined value among the pixels of the reliability image are masked.

6. An ultrasound image generating method which transmits an ultrasonic wave toward a subject, receives a reflected wave, and generates a morphological image representing a shape, the ultrasound image generating method further comprising:

a computer programmed to execute the following steps:
  a sound speed value calculating step of calculating a sound speed value in a region of interest of the morphological image;
  a sound speed image generating step of generating a sound speed image on the basis of the sound speed value of the region of interest;
  a reliability information generating step of generating reliability information of the sound speed value using the sound speed value of each of pixels of the sound speed image;
  a reliability image generating step of generating a reliability image on the basis of the reliability information;
  a display image generating step of generating a display image from at least one of the morphological image, the sound speed image, or the reliability image; and
  a displaying step of displaying the display image,
wherein the reliability information is information obtained from each of pixels of the sound speed image and a predetermined range of pixels including 3×3 pixels around each of the pixels, or measurement error information acquired when a discontinuous point is detected by edge detection processing or gap detection processing on the sound speed image, the sound speed value calculating step has an ambient sound speed value calculating step of calculating an ambient sound speed value, and a local sound speed value calculating step of calculating a local sound speed value on the basis of the ambient sound speed value, and the sound speed value is the local sound speed value, and the sound speed image is a local sound speed image.

7. The ultrasound image generating method according to claim 6,
  wherein the reliability information generating step generates the reliability information for each region corresponding to the region of interest of the sound speed image.

8. An ultrasound image generating method which transmits an ultrasonic wave toward a subject, receives a reflected wave, and generates a morphological image representing a shape, the ultrasound image generating method further comprising:

a computer programmed to execute the following steps:
  a sound speed value calculating step of calculating a sound speed value in a region of interest of the morphological image;
  a sound speed image generating step of generating a sound speed image on the basis of the sound speed value of the region of interest;
  a reliability information generating step of generating reliability information of the sound speed value using the sound speed value of each of pixels of the sound speed image;
  a reliability image generating step of generating a reliability image on the basis of the reliability information;
  a display image generating step of generating a display image from at least one of the morphological image, the sound speed image, or the reliability image;
  a display step of displaying the display image; and
  a sound speed image generating step,
wherein the sound speed value calculating step obtains a focus index value of each of pixels of the morphological image for each of set sound speeds, or obtains an error of a virtual reception wave and a virtual synthesized reception wave in each of the pixels for each of assumed local sound speeds from each of the pixels and a predetermined range of pixels around each of the pixels, and the reliability information generating step generates reliability information on the basis of the focus index value for each of the set sound speeds or the error for each of the assumed local sound speeds, and wherein the sound speed value calculating step calculates an ambient sound speed value or a local sound speed value in a region of interest of the morphological image on the basis of the focus index value for each of the set sound speeds or the error for each of the assumed local sound speeds, the sound speed image generating step generates a sound speed image on the basis of the ambient sound speed value or the local sound speed value corresponding to the region of interest, and the reliability information generating step generates reliability information for each region corresponding to the region of interest of the sound speed image.

9. A non-transitory computer-readable recording medium having the program which causes the computer to execute the steps of the ultrasound image generating method according to claim 6 recorded thereon.

* * * * *